United States Patent [19]
McEwen et al.

[11] Patent Number: 5,873,881
[45] Date of Patent: Feb. 23, 1999

[54] LINEAR DRIVE DERMATOME

[76] Inventors: James Allen McEwen, 10551 Bamberton Drive, Richmond, Canada, V7A 1K6; Geoffrey Fletcher Auchinleck, Suite 302, 1233 Beach Avenue, Vancouver B.C., Canada, V6E 1V4

[21] Appl. No.: 680,590

[22] Filed: Jul. 12, 1996

Related U.S. Application Data

[63] Continuation-in-part of Ser. No. 567,526, Dec. 5, 1995, abandoned.

[51] Int. Cl.[6] .................................................. A61B 17/50
[52] U.S. Cl. ......................... 606/132; 606/131; 30/43.7; 30/182
[58] Field of Search .................................. 606/131, 132, 606/82; 30/43.7, 373, 374, 375, 182, 185

[56] References Cited

U.S. PATENT DOCUMENTS

| | | |
|---|---|---|
| 1,935,605 | 11/1933 | Altruda ..................................... 606/132 |
| 2,288,709 | 7/1942 | Hood . |
| 2,419,114 | 4/1947 | Briegel . |
| 2,435,278 | 2/1948 | Hood . |
| 2,457,772 | 12/1948 | Brown . |
| 2,691,377 | 10/1954 | Hood ....................................... 606/132 |
| 3,327,711 | 6/1967 | Vallis . |
| 3,412,732 | 11/1968 | Simon . |
| 3,428,045 | 2/1969 | Kratzsch et al. . |
| 3,583,403 | 6/1971 | Pohl . |
| 3,670,734 | 6/1972 | Hardy . |
| 3,820,543 | 6/1974 | Vanjushin et al. . |
| 4,211,232 | 7/1980 | Mormann . |
| 4,240,432 | 12/1980 | Mormann . |
| 4,917,086 | 4/1990 | Feltovich et al. . |

*Primary Examiner*—Michael Powell Buiz
*Assistant Examiner*—Tina T. D. Phan
*Attorney, Agent, or Firm*—Hancock Meininger & Porter LLP

[57] ABSTRACT

The dermatome includes a blade assembly comprising a metal blade with fixedly attached thermoplastic carrier. The assembly is releasably mounted to the dermatome housing. A linear drive mechanism-that includes guide members and spring biasing of the blade assembly ensures linear, reciprocating blade movement that prolongs blade life. The linear drive mechanism is housed in a manner that facilitates cleaning and sterilization of the dermatome.

4 Claims, 6 Drawing Sheets

LINEAR DRIVE DERMATOME

This is a continuation-in-part of U.S. patent application Ser. No. 08/567,526 filed Dec. 5, 1995, now abandoned.

FIELD OF THE INVENTION

The present invention relates to a motorized dermatome for cutting thin sections of skin tissue from surgical patients or cadavers, for use in surgical skin grafting procedures. Specifically, the invention provides means for substantially improving the linearity and quality of tissue cutting, while at the same time providing significantly longer blade life and an enclosed housing for improved cleaning and sterilization of the dermatome.

BACKGROUND OF THE INVENTION

Many motorized dermatomes are known in the prior art. Typical examples are described in U.S. Pat. No. 2,419,114 (Briegel), U.S. Pat. No. 2,457,772 (Brown), U.S. Pat. No. 2,787,272 (Groom), U.S. Pat. No. 3,412,732 (Simon), U.S. Pat. No. 3,428,045 (Kratzsch), U.S. Pat. No. 3,670,734 (Hardy), U.S. Pat. No. 3,820,543 (Vanjushin), and U.S. Pat. No. 4,917,086 (Feltovich). All of these devices are fundamentally similar, in that a sharp blade edge is placed in contact with skin and driven by the motor in an oscillatory fashion to create a sawing action. In order to move the blade edge back and forth, the rotational action of the drive motor is converted to more or less linear motion through the use of a number of linkages. A means is usually provided for permitting the blade to cut the skin to a pre-selected depth so that a thin layer of skin can be removed as the dermatome is moved forward.

The cutting characteristics of the dermatome are determined by the motion of the cutting blade. When a blade is cutting tissue, the only useful motion is purely linear. The sawing action of the blade along the axis of the blade edge provides the cutting action while the dermatome is moved forward against the skin to bring more tissue to bear on the blade edge. Any other motion of the blade contributes only to dulling the blade. If the blade is permitted to yaw about an axis perpendicular to the blade edge during its oscillation, the blade edge will be repeatedly pressed into the tissue and withdrawn from tissue during each cycle, having the effect of "hammering" the edge of the blade into a flatter and less sharp shape. If the blade pitches up and down in a direction perpendicular to the direction of the movement of the blade forward along the skin, the blade will be repeatedly scraped across the tissue, having an effect equivalent to "filing" the edge of the blade into a flatter and less sharp shape.

Sharpness of the blade edge is a major variable affecting the quality of tissue cutting and the characteristics of a dermatome. Most dermatomes provide a means for quickly replacing a dull blade during skin grafting surgery in recognition of the fact that blades quickly lose their sharpness. Despite similarities in the materials and process of manufacture of these blades, some dermatomes subjectively seem to remain sharper much longer than others. Loss of sharpness and wearing of the blade is primarily due to the motion of the blade against the tissue.

Relative linearity of blade motion and maintenance of blade sharpness are only two of the factors affecting the performance and ease of use of a dermatome. Another factor of major importance relates to the cleaning of a dermatome between uses, because an improperly or incompletely cleaned dermatome cannot be satisfactorily re-sterilized for reuse. The time, labor-intensivness and resulting quality of cleaning are important aspects of dermatome use and re-use. When a dermatome is used to cut and remove skin, a considerable amount of tissue, debris and other materials will come into contact with the dermatome. As the dermatome must be rigorously cleaned and then re-sterilized between uses, it is desirable that there be no opening in the external surface of the dermatome which allows tissue to come into contact with internal components of the drive mechanism of the dermatome, and which may allow tissue to become entrapped by the internal components of the drive mechanism of the dermatome. However, no dermatome known in the art provides a housing to enclose the internal components of the drive mechanism, which typically converts the rotational motion of a drive source into a more or less linear motion to drive the blade, while at the same time providing means for quickly and easily removing and replacing blades during usage. As a result, cleaning of prior art dermatomes typically requires removal of tissue and debris from the internal region of the dermatome surrounding components of the drive mechanism; such cleaning is very time-consuming and imperfect, resulting in increased labor costs and reduced quality associated with dermatome usage.

An improved dermatome would provide blade oscillation along a perfectly linear path defined by the edge of the blade of the dermatome, while preventing any other motions of the blade with respect to the dermatome body or housing. The blade of the dermatome would be designed to have a low replacement cost and the dermatome body or housing would include a means for quickly and easily replacing the blade during surgery or harvesting of skin from a donor. The drive mechanism would be contained within a housing having no open space in order to reduce the likelihood that tissue and debris would enter into the region of the drive mechanism.

Dermatomes described in the prior art have included a number of attempts to implement and combine some of these desirable characteristics. Brown (U.S. Pat. No. 2,457,772), Groom (U.S. Pat. No. 2,787,272), Simon (U.S. Pat. No. 3,412,732), Kratzsch (U.S. Pat. No. 3,428,045) and Vanjushin (U.S. Pat. No. 3,820,543) all show guide rods intended to limit the motion of a blade carrier to linear motion along a defined axis, to which the blade is attached. These prior-art devices include drive mechanisms which provide accurate translation of the rotational motion of the shaft of a motor into a linear motion of a blade carrier, but none includes means to assure that the dermatome blade engages the blade carrier such that the axis of linear motion of the blade carrier is exactly parallel to the axis of the blade edge. In addition, none of these prior-art dermatomes provides a housing which encloses and surrounds the drive mechanism to prevent the entry of tissue, skin lubricant, and other debris while at the same time permitting quick and easy blade replacement during usage.

The Padgett Dermatome (Padgett Instruments, Kansas) provides for linear motion of the blade by guiding the back edge of the blade against two steel pins, while constraining the blade from pitching motion by guiding it between the dermatome body and a removable width plate. Motion is imparted to the blade by a yoke which pivots on a fixed pin. The yoke, when driven by the motor, swings through a portion of an arc. A pin on the yoke fits into a hole in the blade, while a spring in the yoke holds the blade against the guide pins. Friction and vibration are generated, and efficiency is lost, in the linkage because the rotary motion of the motor is first converted into arcuate motion, and then into linear motion at the blade. This dermatome, while providing excellent linear blade motion, provides reasonably large amplitude blade motion through the use of a very large motor and head, which makes the device unwieldy. In addition, an open space in the dermatome head which enables the yoke pin to engage the blade also enables tissue, skin lubricant, and other debris to enter into the dermatome head and into the region surrounding the yoke and drive mechanism.

The Feltovich dermatome (U.S. Pat. No. 4,917,086) is very similar to the Padgett dermatome, but has a blade assembly comprised of a metal blade non-releasably attached to a thermoplastic blade carrier. The Feltovich dermatome does not include steel guide pins, as included in the Padgett dermatome, to keep the motion of the blade assembly purely linear. Although a smaller and lighter dermatome body and motor make the device easier to handle, the very small amplitude of motion of the blade assembly, as well as the significant non-linearity of motion of the blade assembly, result in a relatively poorer quality of cut, less cutting efficiency, and shorter blade life, for the reasons described above. Also, like the Padgett dermatome, the Feltovich dermatome has an indirect drive, with a yoke component between the motor and the blade assembly which describes an arcuate motion. The arcuate motion of the yoke component generates friction between the yoke and blade assembly, further reducing cutting efficiency, and produces vibration. Also, the motion of the yoke requires an open space in the dermatome head to enable a pin at the end of the yoke to engage the blade assembly, and this open space also enables tissue, skin lubricant, and other debris to enter into the dermatome head and into the region surrounding the yoke and drive mechanism of the Feltovich dermatome. In U.S. patent application Ser. No. 08/256,267, of which the present application is a continuation-in-part, a direct linear drive dermatome for improved cutting of tissue was described, comprising: a blade assembly, including a blade and a blade carrier; a rotational drive assembly; and a housing which engages the blade assembly to constrain the movement of any point on the blade assembly to bi-directional linear movement over a predefined linear range, wherein the engaged blade assembly forms a cover for the housing so that the housing in combination with the engaged blade assembly defines a closed space which surrounds the rotational drive assembly while the blade assembly moves over the predefined linear range. The present invention describes a dermatome having a blade assembly and an alternate drive assembly similar to that used in prior art dermatomes such as the Feltovich dermatome, and a housing which constrains the movement of any point on the blade assembly to bi-directional linear movement over a predefined linear range. In the present invention, the blade assembly in combination with the housing form a cover to define a closed space which surrounds the drive assembly while the blade assembly moves over the predefined linear range. The present invention can be readily implemented by adapting a prior-art dermatome, to produce an improved dermatome having a more linear drive, longer blade life, a better quality of cut and less tissue debris around the drive assembly.

SUMMARY OF THE INVENTION

The present invention provides a dermatome for cutting skin tissue in an improved manner. The invention comprises: a housing including a linear guide face, a guide pin spaced away from and oriented parallel to the linear guide face, a rotational drive for rotating a shaft around a rotational axis and a linear drive mechanism having a spring and a drive pin extending in a direction orthogonal to the rotational axis, wherein the linear drive mechanism is adapted to engage the shaft and convert the rotary motion of the shaft into reciprocating motion of the drive pin and wherein the linear drive mechanism is further adapted so that the spring applies a restoring force to the drive pin when the drive pin is displaced in a direction parallel to the rotational axis and away from the rotational drive; and a blade assembly adapted for selectively attaching to the housing and comprising a metal blade non-removably attached to a thermoplastic blade carrier to define a blade assembly perimeter, the metal blade defining a linear cutting edge located along a side of the blade assembly perimeter and adapted for engagement with skin for removal of the skin in response to reciprocating movement of the metal blade, wherein the blade assembly includes a linear guide slot with sides of equal length which are parallel to the cutting edge and spaced apart from themselves by a slot width and adapted to cooperate with the guide pin of the housing to substantially maintain the reciprocating movement in a direction parallel to the cutting edge, wherein the blade assembly further includes a drive hole adapted to cooperate with and displace the drive pin in a direction away from the rotational drive and further adapted to enable the drive pin to drive the linear cutting edge in reciprocal motion in a direction parallel to the cutting edge when the blade assembly is attached to the housing, and wherein the thermoplastic blade carrier of the blade assembly includes a linear guide formed of a plurality of points on one edge of the thermoplastic blade carrier forming part of the blade assembly perimeter and spaced away from the linear cutting edge by a predetermined distance, wherein that the restoring force applied to the drive pin applies a force to the linear guide of the attached blade assembly in a direction toward the linear guide face of the housing to substantially maintain the reciprocating movement in a direction parallel to the cutting edge.

DESCRIPTION OF THE SPECIFIC EMBODIMENT

Figure 1:
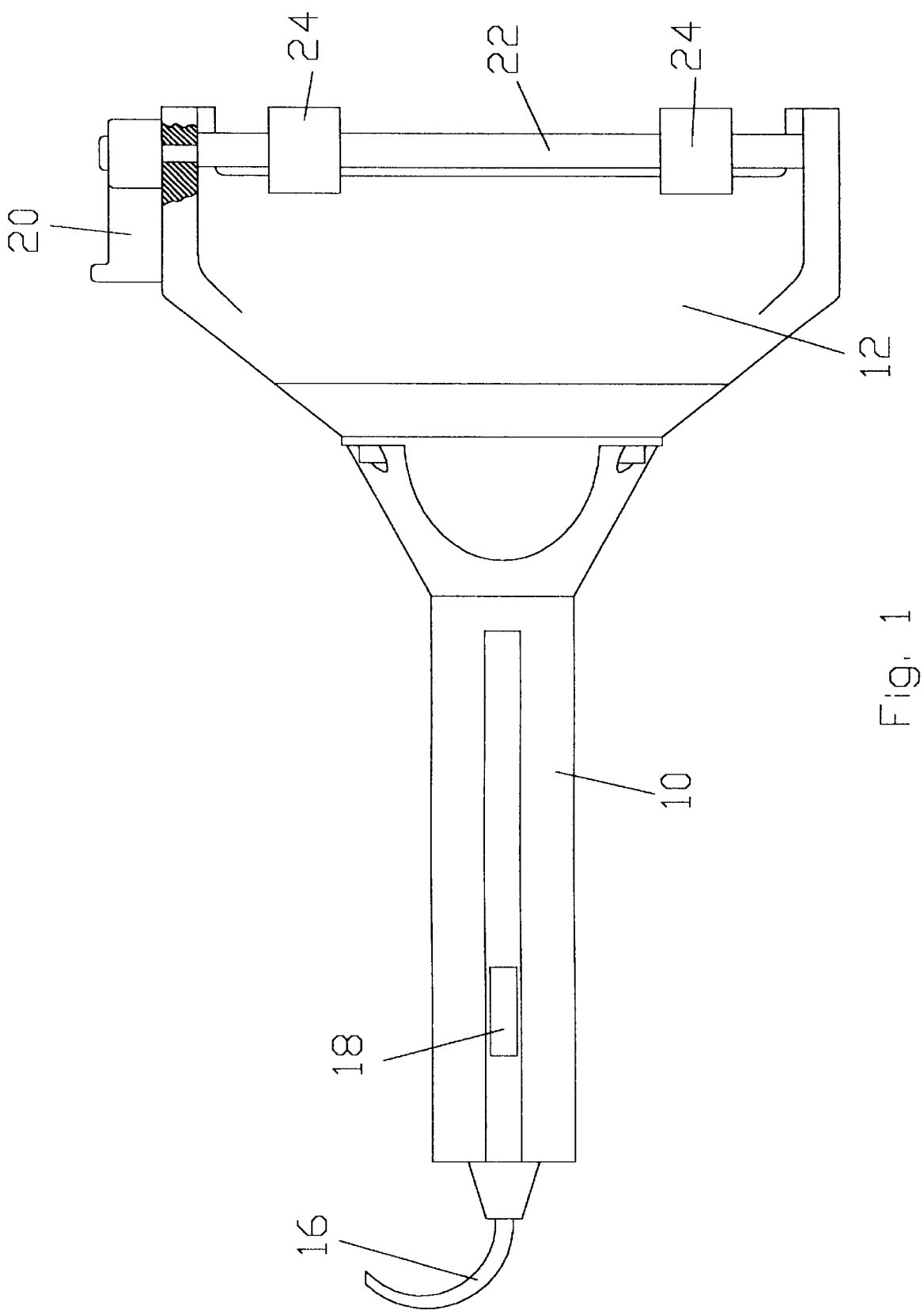
FIG. 1 is a top view of a dermatome according to the invention.

Referring to FIG. 1, the specific embodiment of the dermatome according to the invention is composed of a handle 10, connected to a head 12. Handle 10 encloses motor (not shown in FIG. 1), which is connected to a source of power by cable 16. Switch 18 enables the user to turn on and off motor while operating the dermatome. Head 12 forms part of a housing to enclose the drive mechanism of the dermatome as hereinafter described. Thickness adjustment lever 20 rotates eccentrically mounted shaft 22, which varies the position of bushing 24.

Figure 2:
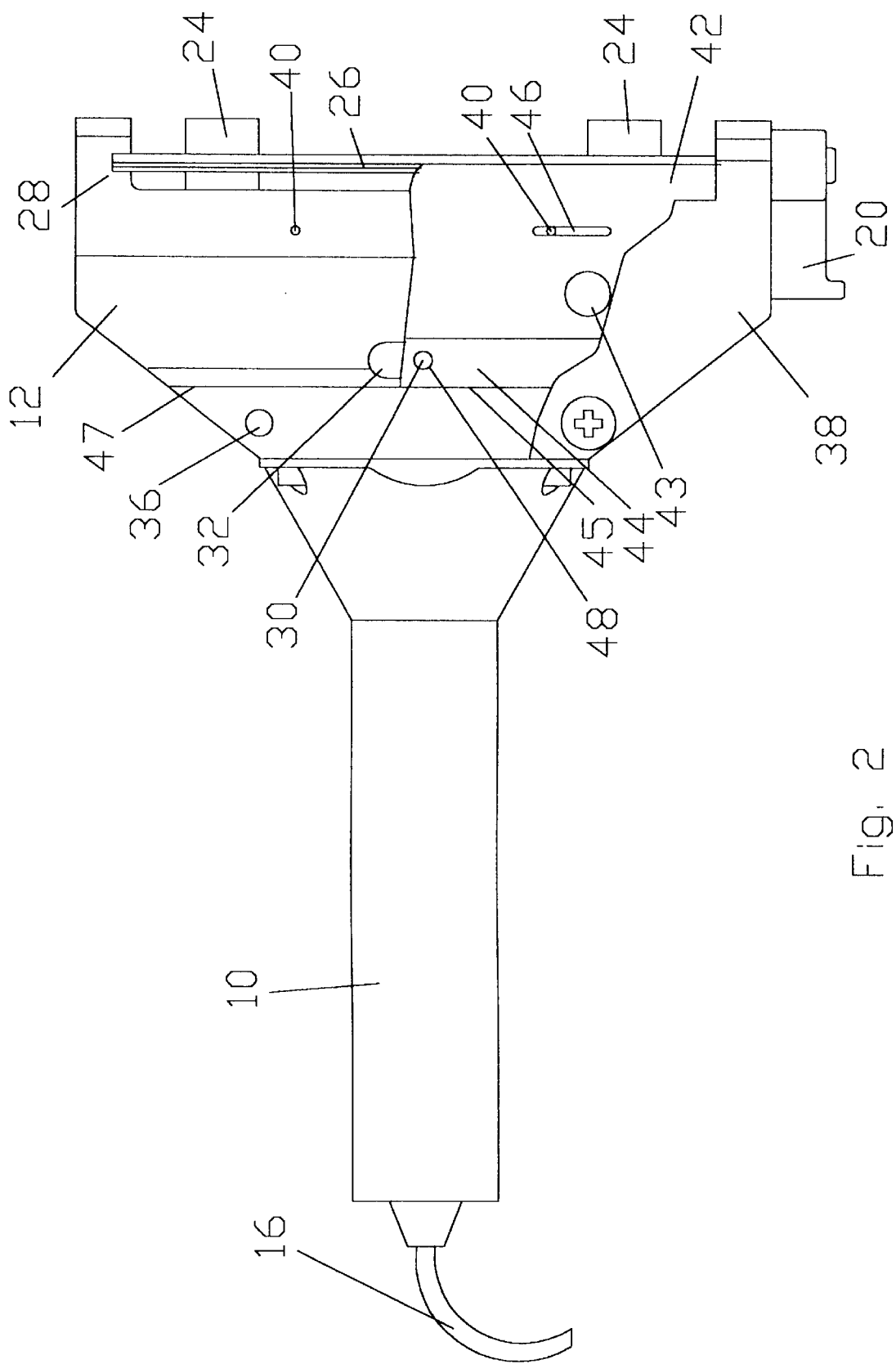
FIG. 2 is a bottom view of the dermatome of FIG. 1 with the blade and width plate shown in partial cutaway for clarity.

Referring to FIG. 2, bushings 24 are connected to thickness guide 26, which is constrained to move within slots 28. Rotation of thickness adjustment lever 20 causes thickness guide 26 to move within the slots.

In the bottom face of head 12 is aperture 32. Aperture 32 provides access to drive pin 30. Threaded holes 36 provide a fastening means for width plate 38 (shown in partial cutaway in FIG. 2). Blade 42 and blade carrier 44 (shown in partial cutaway in FIG. 2) engage guide pins 40 through slots 46. (For clarity, one of slots 46 is shown in FIG. 2.) Drive pin 30 engages blade carrier 44 through hole 48. Blade carrier 44 includes guide edge 45 forming a surface parallel to the cutting edge of blade 42. Guide edge 45 of blade carrier 44 bears on guide face 47 of head 12 when blade carrier 44 is installed in the dermatome. Guide pins 40 engaging slots 46 and guide edge 45 bearing on guide face 47 ensure linear motion of blade carrier 44 and blade 42.

Figure 3:
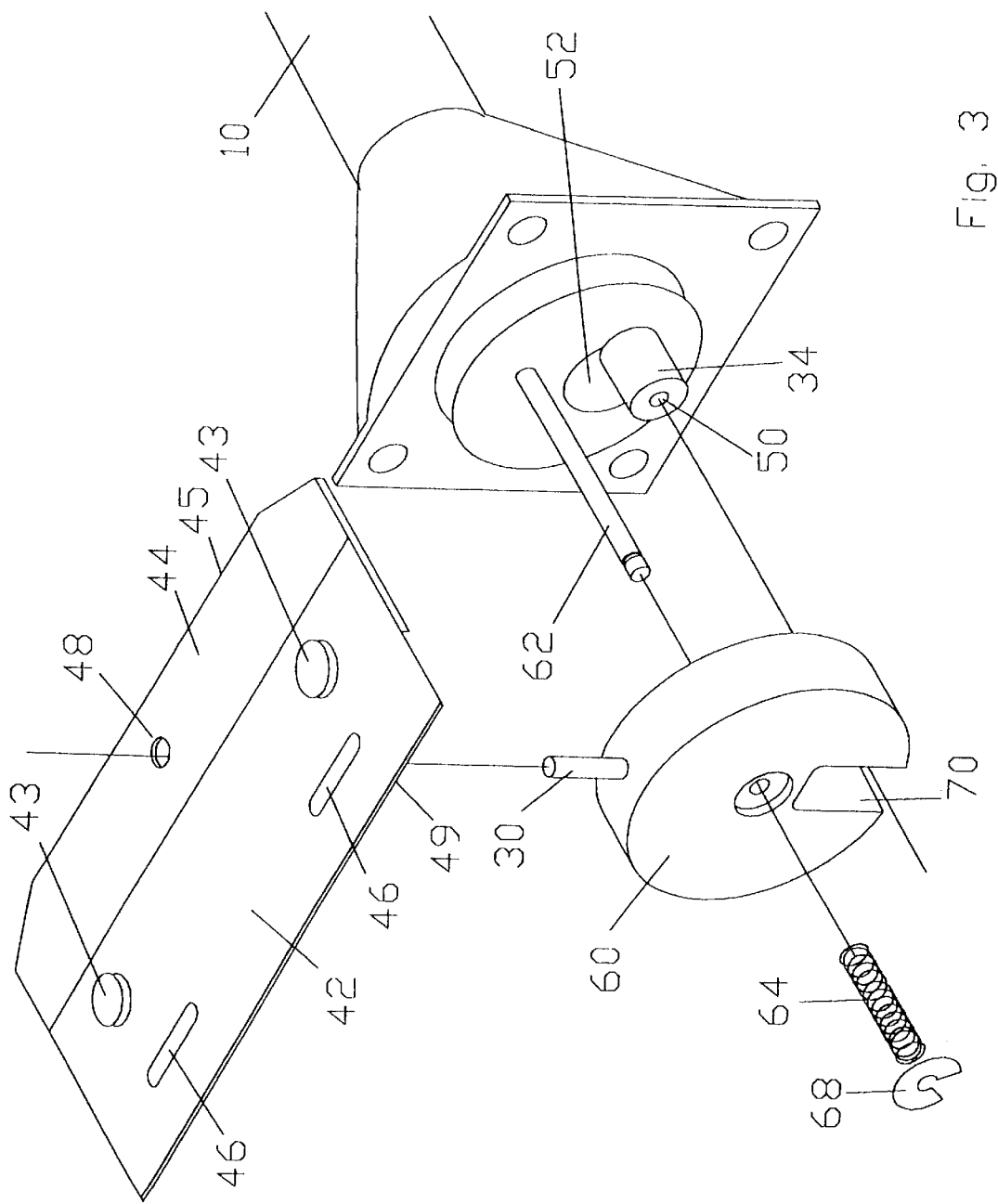
FIG. 3 is an exploded view showing the moving parts of the dermatome of FIG. 1, with the housing not shown for clarity.

FIG. 3 shows the blade assembly, which is comprised of blade 42, which in the preferred embodiment is made of stainless steel, sharpened along edge 49, and blade carrier 44. Blade carrier 44 is rigidly and non-releasably attached to blade 42 with bosses 43 such that blade 42 and blade carrier 44 comprise one rigid part. Blade carrier 44 may be made of thermoplastic material or a lightweight metal such as aluminum, and may be cast, molded or otherwise formed onto blade 42. Blade 42 includes guide slots 46.

Eccentric drive bushing 34 is rotatably attached to shaft 50 on an axis parallel to, but displaced from, the axis of shaft 52 of the determined motor (not shown in FIG. 3) by a predetermined distance, such that operation of motor 14 causes eccentric rotation of eccentric drive bushing 34.

Yoke 60 is rotatably attached to shaft 62 with spring 64 and clip 68, such that slot 70 engages eccentric drive bushing 34. Drive pin 30 forms part of yoke 60. The outside surface 72 of yoke 60 is formed as a partial cylinder having an axis collinear with shaft 62.

When yoke 60 is assembled into housing, the drive motor rotates shaft 52, which causes eccentric drive bushing 34 to rotate within slot 70 of yoke 60. As yoke 60 is constrained to rotate about shaft 62, this causes yoke 60 to oscillate through an arc centered on shaft 62, resulting in oscillator, arcurate motion of drive pin 30.

Figure 4:
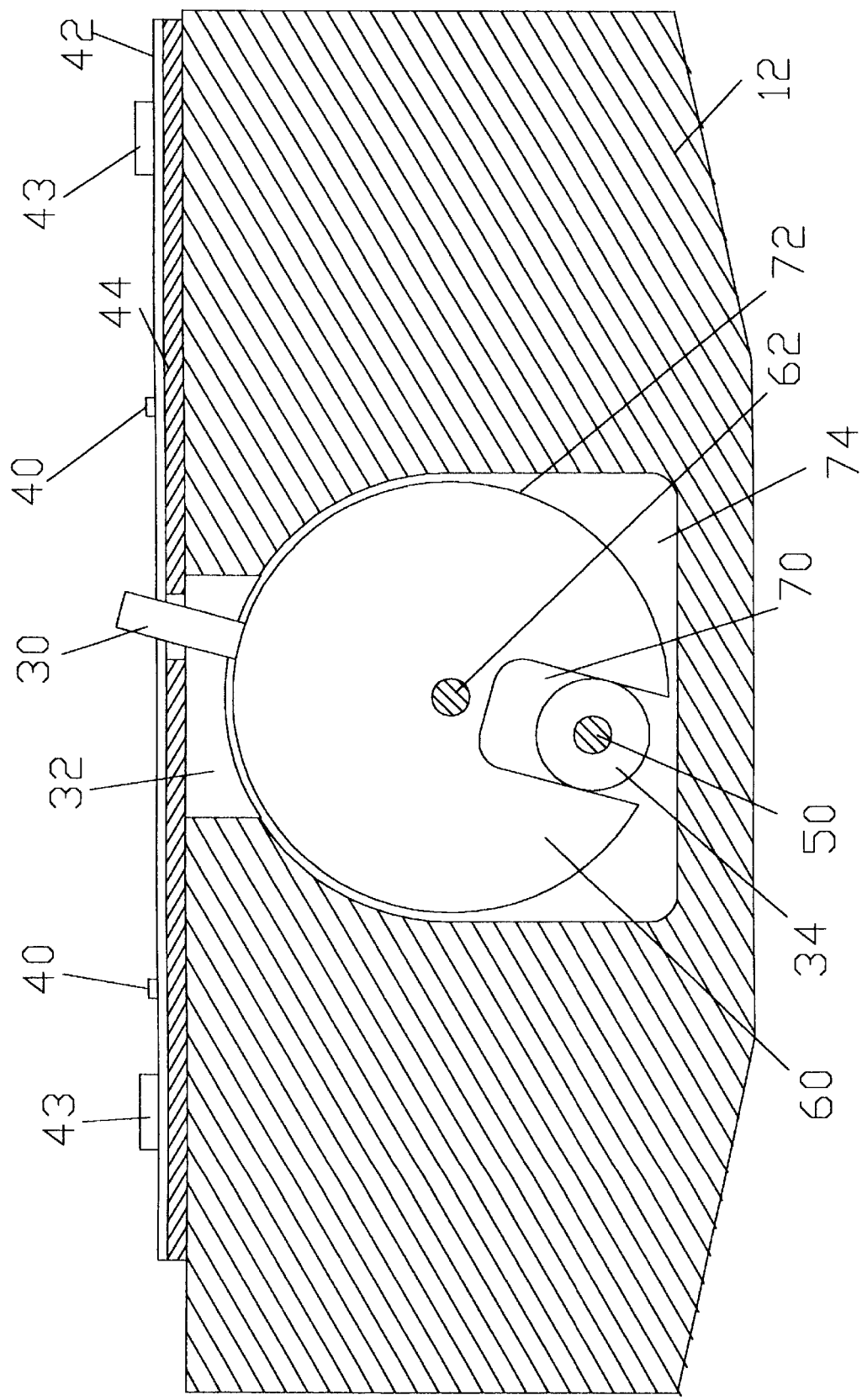
FIG. 4 is a cross section view of the dermatome of FIG. 1.

FIG. 4 shows a cross section through dermatome head 12 looking away from handle 10, as it would be assembled for use. Width plate 38 is omitted for clarity. Blade 42 and blade carrier 44 are fitted over guide pins 40 and drive pin 30. Spring 64 applies restoring force to drive pin 30 which forces slots 46 (not visible in FIG. 4) against guide pins 40, wherein the restoring force applied to the drive pin 30 applies through the drive hole a force to direct the linear guide edge 45 of the blade assembly toward the linear guide face 47 of the housing to substantially maintain reciprocating movement thus ensuring that motion of blade 42 is constrained to the line defined by slots 46 and liners guide face 47.

When assembled, outside surface 72 of yoke 60 engages inside surface 74 of head 12 to form a moveable connection with a very small gap. In this way, ingress of fluid, tissue or other foreign matter into head 12 is prevented.

In the blade assembly of the specific embodiment, blade 42 is formed from stainless steel and blade carrier 44 is formed from inexpensive thermoplastic material non-releasably attached to blade 42, making it cost-effective to remove and discard the blade assembly after use on individual patients or cadavers, thus eliminating the need to clean and re-sterilize the blade assembly.

Figure 5A:
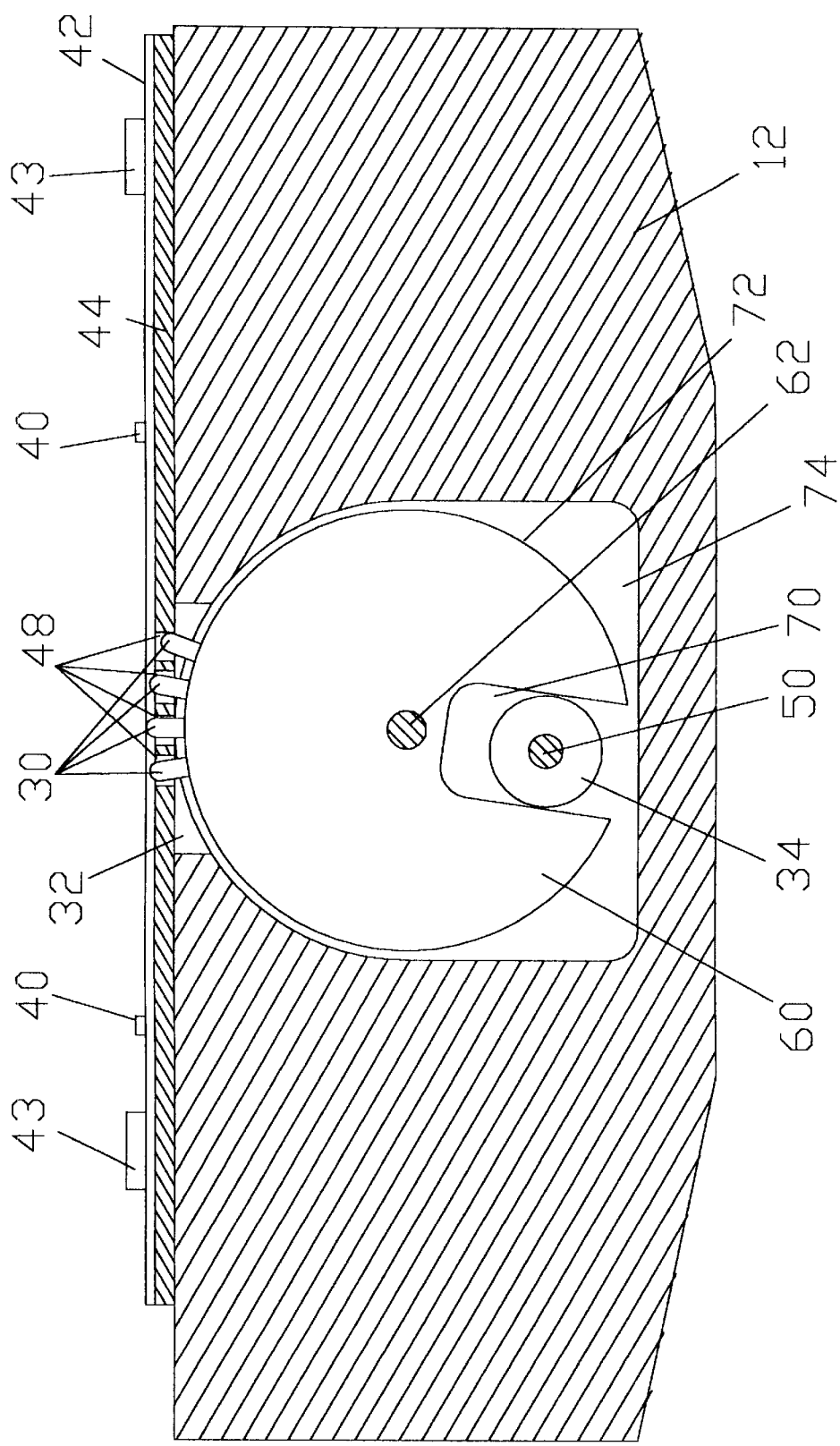
FIGS. 5a and 5b are cross section views of two alternate rotational drive mechanisms for the dermatome of FIG. 1.

FIG. 5a shows an alternate means for engaging blade carrier 44 and drive pin 30. In this embodiment, a number of drive pins 30 engage a number of holes 48 in blade carrier 44. In this way, at least one of drive pins 30 engages a hole 48 during the entire arcurate motion of yoke 60. This eliminates the need for a large hole 48 and a long pin 30 and thus prevents premature wear of the hole in carrier 44.

Figure 5B:
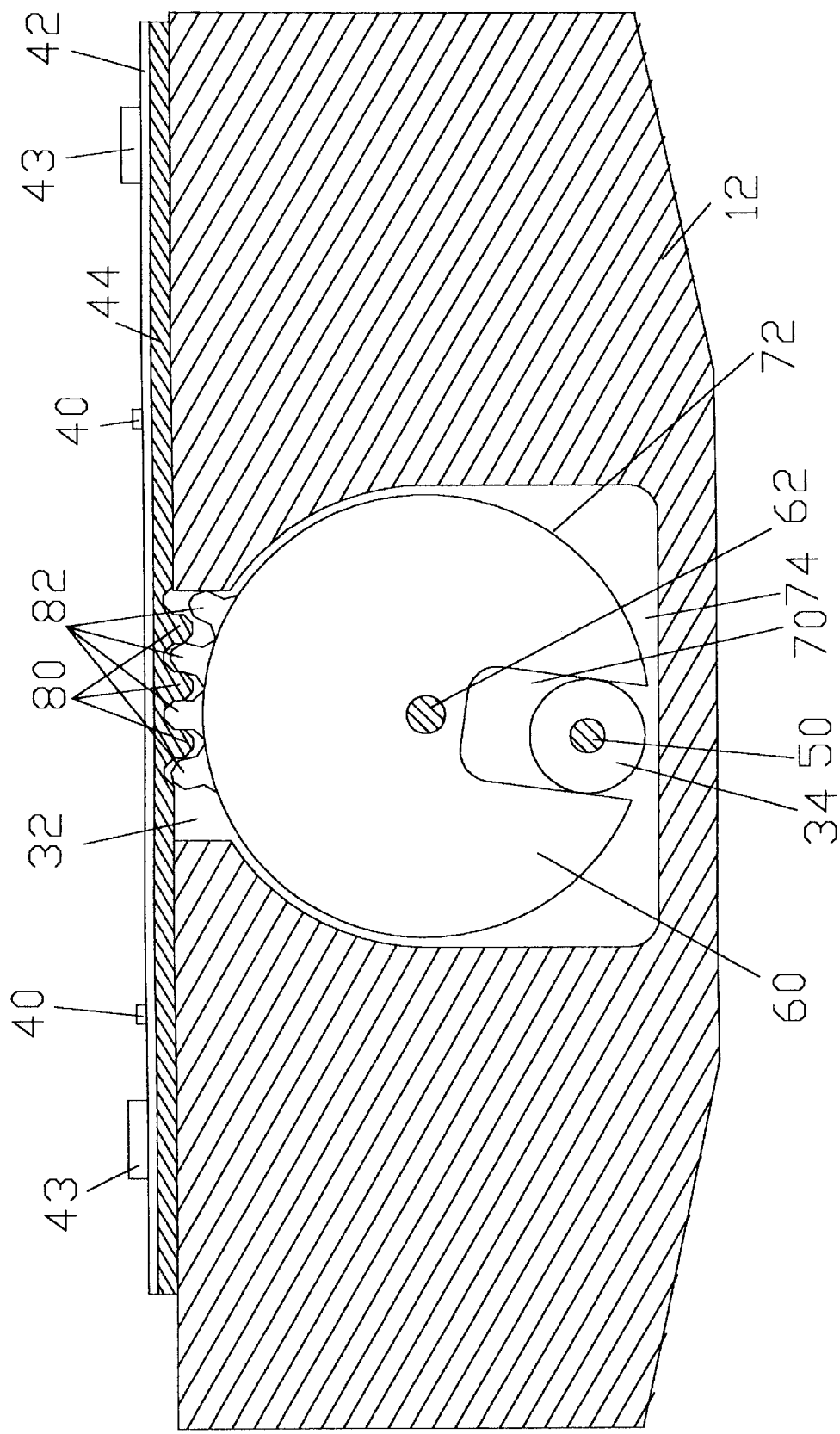

FIG. 5b shows another means for engaging blade carrier 44 and yoke 60. In this embodiment, the underside of blade carrier 44 includes molded teeth 80 which engage drive teeth 82 on yoke 60. In this embodiment, the drive teeth on yoke 60 convert the arcurate motion of yoke 60 to linear motion of blade carrier 44 in the same manner as a common rack and pinion gear. This mechanism eliminates the need for any holes in blade carrier 44, thereby eliminating wear in the linkage.

Typical Use of the Dermatome When the dermatome is assembled as shown in FIGS. 1 and 2, the front edge of blade 42 is directly below thickness guide 26. The user may now rotate thickness adjustment lever 20 to adjust the space between the edge of blade 42 and thickness guide 26 until the desired skin graft thickness is set.

To use the dermatome, the edge of blade 42 is placed in contact with the donor tissue, switch 18 is activated and the dermatome is moved forward. The oscillation of blade 42 cuts a thin layer of tissue which is lifted over the top of blade 42 and may be removed.

Many modifications and variations of the mechanisms described are possible without departing from the principles of the invention, therefore the invention should be limited only by the scope of the appended claims.

We claim:

1. A dermatome for cutting skin tissue comprising:

a dermatome housing including a linear guide face, a shaft having a rotational axis, a rotational drive for engaging the shaft and rotating the shaft around the rotational axis, and a linear drive mechanism having a spring, and a drive pin that extends in a direction orthogonal to the rotational axis, wherein the linear drive mechanism includes a rotatable yoke member to engage the shaft and convert the rotary motion of the shaft into reciprocating, rotational motion of the drive pin, and wherein the linear drive mechanism is further adapted so that the spring applies a restoring force to the drive pin when the drive pin is displaced in a direction parallel to the rotational axis and away from the rotational drive; and a blade assembly adapted for selective attachment to the dermatome housing and comprising a metal blade non-removably attached to a thermoplastic blade carrier, the metal blade including a linear cutting edge adapted for engagement with skin for removal of the skin in response to reciprocating movement of the metal blade, the thermoplastic blade carrier including a drive hole having a shape and location adapted to cooperate with the reciprocating, rotating drive pin and to enable the drive pin to move the blade carrier and attached blade in reciprocal motion in a direction parallel to the cutting edge when the blade assembly is attached to the dermatome housing, and including a linear guide parallel to the linear cutting edge of the non-removably attached blade, wherein the restoring force applied to the drive pin applies a force through the cooperating drive hole of the blade carrier to direct the linear guide of the blade carrier toward the linear guide face of the dermatome housing to moveably engage the linear guide face in order to substantially maintain the reciprocal motion of the blade carrier in a direction parallel to the cutting edge.

2. The dermatome of claim 1 wherein the linear guide face is a flat surface parallel to the linear cutting edge and spaced away from the linear cutting edge by a predetermined distance.

3. The dermatome of claim 1 wherein the linear guide face is an edge of one side of the perimeter of the thermoplastic blade carrier and spaced away from the linear cutting edge by a predetermined distance.

4. A dermatome for cutting skin tissue comprising:

a dermatome housing including a linear guide face, two guide pins spaced away from and oriented parallel to the linear guide face, a rotational drive for rotating a shaft around a rotational axis and a linear drive mechanism having a spring, and a drive pin extending in a direction orthogonal to the rotational axis, wherein the linear drive mechanism includes a yoke member that is adapted to engage the shaft and convert the rotary motion of the shaft into reciprocating motion of the drive pin and wherein the linear drive mechanism is further adapted so that the spring applies a restoring force to the drive pin when the drive pin is displaced in a direction parallel to the rotational axis and away from the rotational drive; and a blade assembly adapted for selectively attaching to the dermatome housing and comprising a metal blade non-removably attached to a thermoplastic blade carrier to define a blade assembly perimeter, the metal blade defining a linear cutting edge located along a side of the blade assembly perimeter and adapted for engagement with skin for removal of the skin in response to reciprocating movement of the metal blade, wherein the metal blade includes a pair of spaced-apart linear guide slots, each slot with sides of equal length which are parallel to the cutting edge and adapted to cooperate with one of the guide pins of the dermatome housing to substantially maintain the reciprocating movement in a direction parallel to the cutting edge, the thermoplastic blade carrier including a drive hole adapted to cooperate with the drive pin to enable the drive pin to drive the linear cutting edge in reciprocal motion in a direction parallel to the cutting edge when the blade assembly is attached to the dermatome housing, and including a linear guide formed of a continuous edge on the blade assembly perimeter and spaced away from the linear cutting edge by a predetermined distance, wherein the restoring force applied to the drive pin applies a force to the linear guide of the attached blade assembly in a direction toward the linear guide face of the dermatome housing in order to substantially maintain the reciprocating movement in a direction parallel to the cutting edge.

\* \* \* \* \*